US008562643B2

(12) United States Patent
Tekulve et al.

(10) Patent No.: US 8,562,643 B2
(45) Date of Patent: Oct. 22, 2013

(54) SELF CLOSING OCCULSION DEVICE WITH A TWIST

(75) Inventors: Kurt J. Tekulve, Ellettsville, IN (US); Carrie Fercik, Ellettsville, IN (US); Elizabeth Theobald, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 260 days.

(21) Appl. No.: 13/091,750

(22) Filed: Apr. 21, 2011

(65) Prior Publication Data

US 2012/0271348 A1  Oct. 25, 2012

(51) Int. Cl.
*A61B 17/08* (2006.01)
(52) U.S. Cl.
USPC ........................................ 606/213
(58) Field of Classification Search
USPC ........... 606/95, 108, 151, 157, 158, 191, 213, 606/232; 623/1.1; 128/831
See application file for complete search history.

(56) References Cited

U.S. PATENT DOCUMENTS

| 5,725,552 | A | 3/1998 | Kotula et al. |
| 5,846,261 | A | 12/1998 | Kotula et al. |
| 5,944,738 | A | 8/1999 | Amplatz et al. |
| 6,123,715 | A | 9/2000 | Amplatz |
| 2007/0056591 | A1* | 3/2007 | McSwain ...................... 128/831 |
| 2012/0065667 | A1* | 3/2012 | Javois et al. .................. 606/213 |
| 2012/0316597 | A1* | 12/2012 | Fitz et al. ..................... 606/191 |

OTHER PUBLICATIONS

"PFO Occluder", *AGA Medical Corporation* publication, Mar. 2005, 2 pages.
"Amplatzer Septal Occluder and Delivery System", *AGA Medical Corporation*, dated Feb. 2010, 15 pages, obtained at the internet address: http://www.amplatzer.com/portals/aga/uploaded_docs/600208-008_ASD_eIFU_secure_for_website.pdf.

* cited by examiner

*Primary Examiner* — Julian W Woo
(74) *Attorney, Agent, or Firm* — Brinks Hofer Gilson & Lione (57) ABSTRACT

An occlusion device and a method for occluding an opening in a body tissue with the occlusion device are provided. The occlusion device comprises a middle portion, a distal portion, and a proximal portion. The middle portion may be formed of non-woven wires and twisted about the longitudinal axis. The distal portion and the proximal portion may be comprised of a shape memory material. The occlusion device may be shape set to establish a preset configuration, and thus may be deformable to fit in and occlude the opening in the body tissue.

21 Claims, 6 Drawing Sheets

SELF CLOSING OCCULSION DEVICE WITH A TWIST

BACKGROUND

1. Field of the Invention

The present disclosure generally relates to medical devices. More specifically, the present disclosure relates to occlusion devices for occluding openings in body tissue.

2. Description of the Related Art

Various medical conditions involve openings such as punctures, holes, or tunnels in body tissue, for example in a septum or other body tissue. Examples of such defects include atrial septal defects (ASDs), ventricular septal defects (VSDs), patent foramen ovales (PFOs), or a patent ductus arteriosus (PDA). These defects allow fluid communication between cavities on either side of the body tissue.

Several devices have been developed to occlude these defects, for example the Amplatzer Septal Occluder, Gore Helex Septal Occluder, and Occlutech Figula. The Amplatzer design, disclosed in U.S. Pat. Nos. 5,725,552, 5,846,261, 5,944,738, and 6,123,715, has braided and woven nitinol wires that are shape set into two discs with a thinner middle portion, such that the middle portion is placed through the opening and the two discs clamp down on each side of the body tissue. The other devices are similarly designed.

However, these devices may be difficult to adapt to a variety of short and long tunnel widths. The devices may be improved to more effectively provide a constant inward axial pressure on each side of the body tissue. Although adequate, these devices may be improved to provide a more effective fit and grip for a variety of openings.

SUMMARY

In overcoming the drawbacks and other limitations of the related art, the present disclosure provides an occlusion device with a non-woven middle portion for occluding an opening in a body tissue. The occlusion device may apply consistent pressure without clamping down on the body tissue and may work in a wider variety of opening widths, because the non-woven middle portion may more easily expand and contract axially, and because in some embodiments the diameter of the middle portion may not deform significantly during axial expansion and contraction.

In some embodiments, the present disclosure relates to an occlusion device for occluding an opening in a body tissue. The occlusion device comprises a middle portion having a distal end extending to an opposing proximal end to define a longitudinal axis of the device. The middle portion is formed of non-woven wires and twisted about the longitudinal axis. The middle portion has a preset middle diameter. The occlusion device further comprises a distal portion that is attached to the distal end of the middle portion. The distal portion has a preset distal diameter and is made of a shape memory material. The occlusion device further comprises a proximal portion that is attached to the proximal end of the middle portion. The proximal portion has a preset proximal diameter and is made of a shape memory material. The preset middle diameter is less than each of the preset distal diameter and the preset proximal diameter. Each of the preset middle, distal, and proximal diameters is perpendicular to the longitudinal axis.

In some embodiments, the present disclosure relates to a method for occluding an opening in a body tissue with an occlusion device. The method comprises providing the occlusion device deployed from an inner member at the opening in the body tissue. The method further comprises collapsing the occlusion device into a collapsed configuration. The method further comprises delivering the occlusion device to the opening.

In some embodiments, the present disclosure relates to a delivery assembly for placing and retrieving an occlusion device for occluding an opening in a body tissue. The assembly comprises an outer sheath having a tubular body extending from a proximal part to a distal part. The tubular body includes a sheath lumen extending therethrough. The assembly further comprises an inner member extending from a proximal portion to a distal portion. The inner member is disposed within the sheath lumen and configured for axial movement relative to the outer sheath. The assembly further comprises the occlusion device being coaxially disposed within the sheath lumen, removably coupled to the distal portion of the inner member, and deployable through the distal part of the outer sheath by means of the relative axial movement of the inner member.

In some embodiments, the present disclosure relates to a method of forming an occlusion device for occluding an opening in a body tissue. The method comprises forming from a shape memory material a distal portion of the occlusion device and a proximal portion of the occlusion device. The method further comprises forming from non-woven shape memory material wires a middle portion of the occlusion device. The middle portion has a distal end attached to the distal portion and extends to an opposing proximal end attached to the proximal portion to define a longitudinal axis. The method further comprises twisting the middle portion about the longitudinal axis. The method further comprises shape setting the distal portion to establish a preset distal diameter, the proximal portion to establish a preset proximal diameter, and the twisted middle portion to establish a preset middle diameter. The preset middle diameter is less than each of the preset distal and proximal diameters. Each of the preset distal, proximal, and middle diameters is perpendicular to the longitudinal axis.

Further features and advantages of the present disclosure will become apparent from consideration of the following description and the appended claims when taken in connection with the accompanying drawings. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The present disclosure generally provides an occlusion device for occluding an opening in a body tissue, and a method for occluding an opening in a body tissue with the occlusion device. Embodiments of the present disclosure provide a more effective way of treating openings in body tissue. For example, the occlusion device may comprise a twisted middle portion comprised of non-woven wires. Due to the deformability of the twisted middle portion, the occlusion device can be more effectively deployed in relatively short and long opening widths, and can also more effectively apply consistent pressure to each side of the body tissue.

The terms "substantially" used herein with reference to a quantity includes variations in the recited quantity that are equivalent to the quantity recited, such as an amount that is insubstantially different from a recited quantity for an intended purpose or function. The term "woven wires" used herein is defined as wires interlaced together so as to overlap each other. The term "braided wires" used herein is defined as three or more wires interweaved in an overlapping pattern. In all instances, the term "diameter" can be replaced with "cross sectional area" with the associated change of meaning. As used herein, the term "preset" plus a length or area quantity is defined as a length or area while no external forces are applied, and is not limited to lengths or areas established by shape-setting.

Figure 1A:
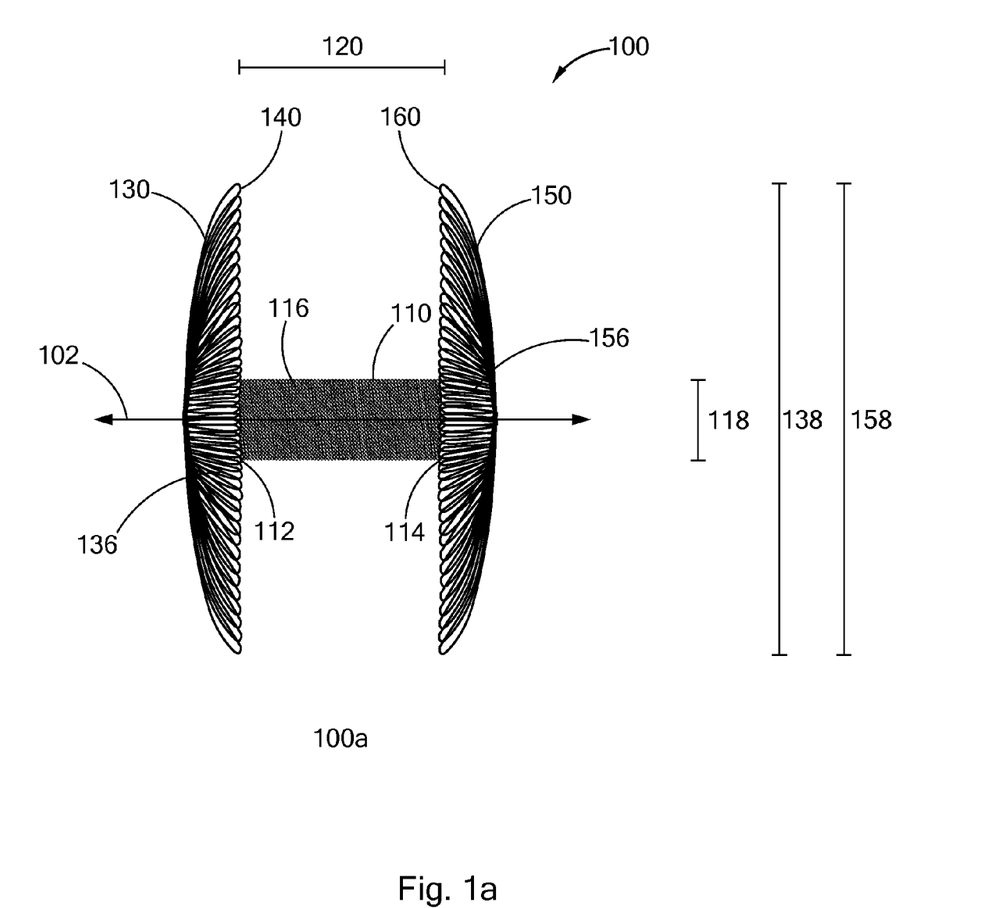
FIG. 1a is a side view of an occlusion device with a twisted middle portion in a preset configuration in accordance with some embodiments of the present disclosure.

FIG. 1a illustrates an occlusion device 100 in a preset configuration 100a with a twisted middle portion 110, a distal portion 130, and a proximal portion 150, in accordance with some embodiments of the present disclosure. The middle portion 110 may have a distal end 112 extending to an opposing proximal end 114 to define a longitudinal axis 102 of the occlusion device 100. The middle portion 110 may be initially formed of a plurality of straight and/or parallel wires 116 that extend from the distal end 112 to the proximal end 114. The middle portion 110 may then be twisted to form a spiral shape that extends from the distal end 112 to the proximal end 114. The wires 116 may thus be formed of wires that spiral about the longitudinal axis 102 and extend from the distal end 112 to the proximal end 114. Both before and after twisting of the middle portion 110, the wires 114 may be one or both of non-woven and/or non-braided. The twist direction (chirality) may be chosen as left-handed or right-handed, depending on which twist direction makes the occlusion device 100 better fit a target opening.

The distal portion 130 may be formed of a distal set of wires 136, and the proximal portion 150 may be formed of a proximal set of wires 156. The distal and the proximal sets of wires 136 and 156 may each be one or both of woven or braided. In some embodiments, the distal portion 130 may be attached to and/or integral with the distal end 112 of the middle portion 110, and the proximal portion 150 may be attached to and/or integral with the proximal end 114 of the middle portion 110. For example, the wires 116, 136, and/or 156 may include individual wires that extend through one, two, or all of the middle, distal, and proximal portions 110, 130, and 150. An individual wire may extend through the distal portion 130 and be among the wires 136 and woven with other individual wires of the wires 136. The same individual wire may then extend through the middle portion 110, being among, for example, the spiraling, parallel, non-woven wires 116. The same individual wire may then extend through the proximal portion 150 and be among the wires 156 and woven with other individual wires of the wires 156. In other embodiments, the wires 116 may be different wires than the wires 136 and 156. For example, the distal and proximal ends 112 and 114 of the wires 116 may, when initially straight and parallel, be respectively soldered onto the wires 136 and 156. After soldering is complete, the wires 116 may then be twisted.

The wires 116, 136, and 156 of the occlusion device 100 may be formed from any suitable material such as a superelastic material, high density polymeric material, stainless steel wire, cobalt-chromium-nickel-molybdenum-iron alloy, cobalt-chrome, copper-zinc-aluminum, or copper-aluminum-nickel alloy. It is understood that in some implementations the 116, 136, and 156 may be formed of any other suitable material that will result in a self-coiling device, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives.

In some embodiments, the wires 116, 136, and 156 are made from Nitinol with a transition temperature that is below normal body temperature of humans (i.e., below 98.6° F.). Thus, when the occlusion device 100 is deployed in a body vessel and exposed to normal body temperature, the alloy in the occlusion device 100 transforms to austenite, such that the device returns to its remembered state, which for the present disclosure may be the preset configuration 100a.

In other embodiments, the distal and proximal portions 130 and 150 may not be formed of the wires 136 and 156. The distal and proximal portions 130 and 150 may be formed of collagen, biomaterials, or a laser cut Nitinol frame. The term "shape memory material" is intended to encompass all of these materials, in addition to the shape memory alloys mentioned earlier. Moreover, shape memory materials are not limited those described in this specification.

The materials forming the middle, distal, and proximal portions 110, 130, and 150 may allow the middle, distal, and proximal portions 110, 130, and 150 to expand and contract, as will be described in more detail.

In some embodiments, the occlusion device 100 may be shape set after the untwisted middle portion has been twisted into the twisted middle portion 110. The shape setting results in the preset configuration 100a of the occlusion device 100 with the middle portion 110 having a preset middle diameter 118 and a preset middle length 120, the distal portion 130 having a preset distal diameter 138, and the proximal portion 150 having a preset proximal diameter 158. The middle portion 110 may have a tubular shape, with the preset middle diameter from the distal end 112 to the proximal end 114. The preset middle, distal, proximal diameters 118, 138, and 158 may be perpendicular to the longitudinal axis 102, and the preset middle length 120 may be parallel to the longitudinal axis 102.

If the occlusion device 100 has elastic or superelastic properties, an external force applied to the occlusion device 100 may expand, contract, or deform the device 100 away from its preset configuration 100a. However, if the device 100 has a shape memory property, the occlusion device 100 may have a tendency to return to its preset configuration 100a. Temperature changes may change the preset configuration 100a. For example, a change from room temperature to body temperature may cause the middle portion 110 to contract and/or experience an inward torque and thus reduce the preset middle length 120.

In some embodiments, the preset middle diameter 118 may be less than each of the preset distal and proximal diameters 138 and 158. The preset distal and proximal diameters 138 and 158 may be substantially equal. For example, the occlusion device 100 may be substantially shaped as a dumbbell. In other embodiments (not pictured), one of the preset distal and proximal diameters 138 and 158 may be greater than the other, with both being greater than the preset middle diameter 118.

The preset middle length 120 may have any fractional, decimal or integral value between 2 and 12 millimeters, for example. The preset middle diameter 118 may have any fractional, decimal or integral value between 4 and 38 millimeters, for example. Each of the preset distal diameter 138 and the preset proximal diameter 158 may have any fractional, decimal or integral value between 12 and 54 millimeters, for example. The preset proximal diameter 138 and the preset proximal diameter 158 may have values different from one another, with each value selected from the above range, for example.

The twisting of the middle portion 110 may cause the preset middle diameter 118 to be lower than an initial pre-twisting diameter. For example, the initial pre-twisting diameter may be equal to the preset distal and proximal diameters 138 and 158. However, after twisting the middle portion 110, the preset middle diameter 118 may be less than each of the preset distal and proximal diameters 138 and 158.

In some embodiments, each of the distal portion 130 and the proximal portion 150 may have a disc shape. In some embodiments, each of the distal portion 130 and the proximal portion 150 may respectively have on their ends that attach to the middle portion 110 a distal flat surface 140 and a proximal flat surface 160 that are respectively configured to be applied to a distal side and a proximal side of the body tissue. In some embodiments (not pictured), each of the distal portion 130 and the proximal portion 150 may respective have on their ends that attach to the middle portion 110 a distal concave surface and a proximal concave surface that are respectively configured to be applied to a distal side and a proximal side of the body tissue.

Each of the distal portion 130 and the proximal portion 150 may have preset distal and proximal diameters 138 and 158 at the ends that attach to the middle portion 110 (i.e. the interior ends), wherein the diameters taper outwardly in the directions opposite the middle portion 110. In other embodiments (not pictured), each of the distal portion 130 and the proximal portion 150 may have in their middle areas preset distal and proximal diameters 138 and 158 that taper in the directions toward the middle portion 110, and also taper in the directions opposite the middle portion 110.

Figure 1B:
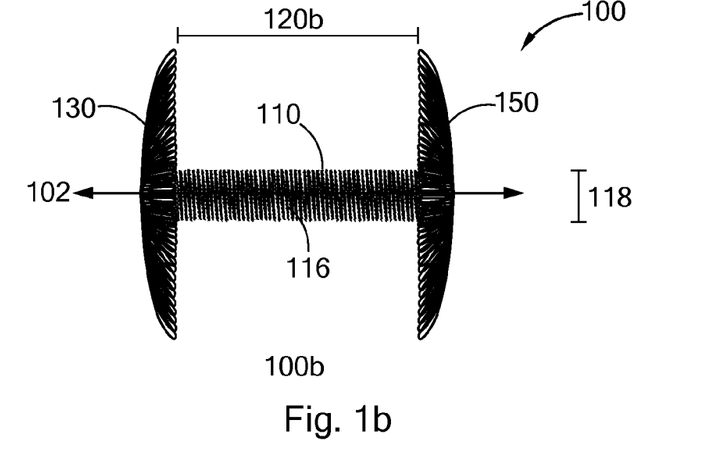
FIG. 1b is a side view of the occlusion device of FIG. 1a with the twisted middle portion in an expanded configuration in accordance with some embodiments of the present disclosure.

FIG. 1b illustrates the occlusion device 100 in an axially expanded configuration 100b in accordance with some embodiments of the present disclosure. An external axial expanding force applied to the middle portion 110 may expand the middle portion 110 along the longitudinal axis 102 into the axially expanded configuration 100b with an axially expanded length 120b. Releasing the middle portion 110 from the axially expanded configuration 100b by ending the axial expanding force and applying no further external forces may cause the middle portion 110 to contract along the longitudinal axis 102 back into the preset configuration 100a of the occlusion device 100. The contraction may decrease the spacing between the spirals and/or stretch the wires of the middle portion 110. The contraction may also cause an inward torque, causing the attached distal portion 130 and proximal portion 150 to torque inwardly and thus closer together.

Figure 1C:
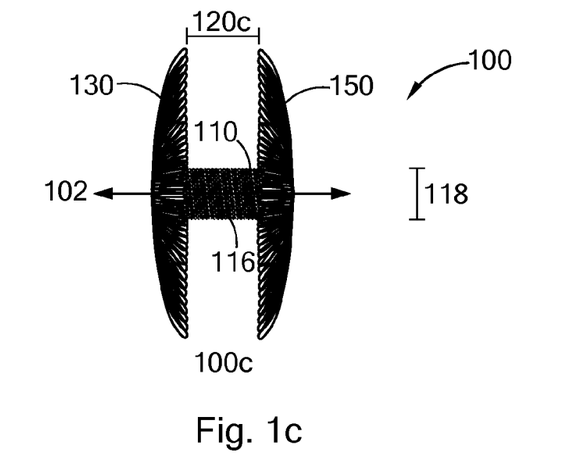
FIG. 1c is a side view of the occlusion device of FIG. 1a with the twisted middle portion in a collapsed configuration in accordance with some embodiments of the present disclosure.

FIG. 1c illustrates the occlusion device 100 in an axially contracted configuration 100c in accordance with some embodiments of the present disclosure. An external axial contracting force applied to the middle portion 110 may contract the middle portion 110 along the longitudinal axis 102 into the axially contracted configuration 100c with an axially contracted length 120c. Releasing the middle portion 110 from the axially contracted configuration 100c by ending the external axial contracting force and applying no further external forces may cause the middle portion 110 to expand along the longitudinal axis 102 back into the preset configuration 100a of the occlusion device 100. The expansion may increase the spacing between the spirals and/or stretch the wires of the middle portion 110. The contraction may also cause an outward torque, causing the attached distal portion 130 and proximal portion 150 to torque outwardly and thus move further from each other.

In some embodiments, because the twisted middle portion 110 has a spiral shape formed from non-woven wires 116, the middle portion 110 may be axially expanded and contracted while substantially maintaining the preset middle diameter 118, or deforming to a lesser extent than if the middle portion 110 was formed of woven and braided wires. In other embodiments, however, the preset middle diameter 118 may significantly decrease upon axial expansion and/or significantly increase upon axial contraction of the middle portion 110.

Figure 1D:
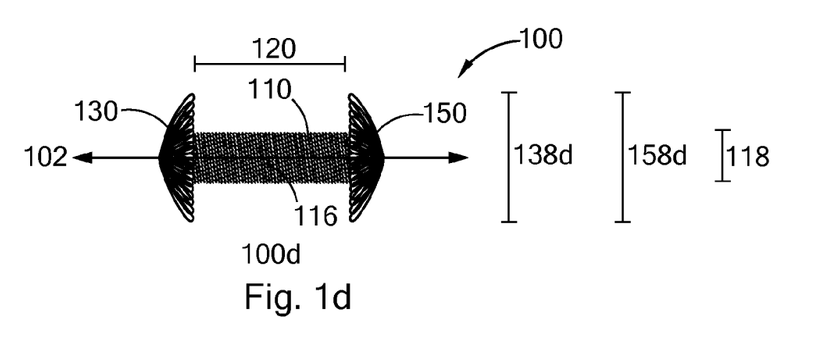
FIG. 1d is a side view of the occlusion device of FIG. 1a with the distal portion in a contracted configuration in accordance with some embodiments of the present disclosure.

FIG. 1d illustrates the occlusion device 100 in a collapsed configuration 100d in accordance with some embodiments of the present disclosure. An external radial contracting force applied to the occlusion device 110 may contract the distal portion 130 and the proximal portion 150 in a direction perpendicular the longitudinal axis 102 into the collapsed configuration 100d, with the distal portion 130 and the proximal portions 150 achieving radially contracted distal and proximal diameters 138d and 158d. Releasing the distal portion 130 and the proximal portion 150 from the radially contracted configuration 100d by ending the external radial contracting force and applying no further external forces may cause the distal portion 130 and the proximal portion 150 to expand along the longitudinal axis 102 back into the preset configuration 100a of the occlusion device 100. In some embodiments (not pictured), the middle portion 118 may also be contracted to a contracted diameter 118d. In other embodiments (not pictured), one but not the other of the distal portion 130 and the proximal portion 150 may be contracted. Moreover, the collapsed configuration 100d is not limited to the embodiments described herein. One skilled in the art will recognize other ways to collapse the occlusion device 100 for deployment at an opening.

Figure 1E:
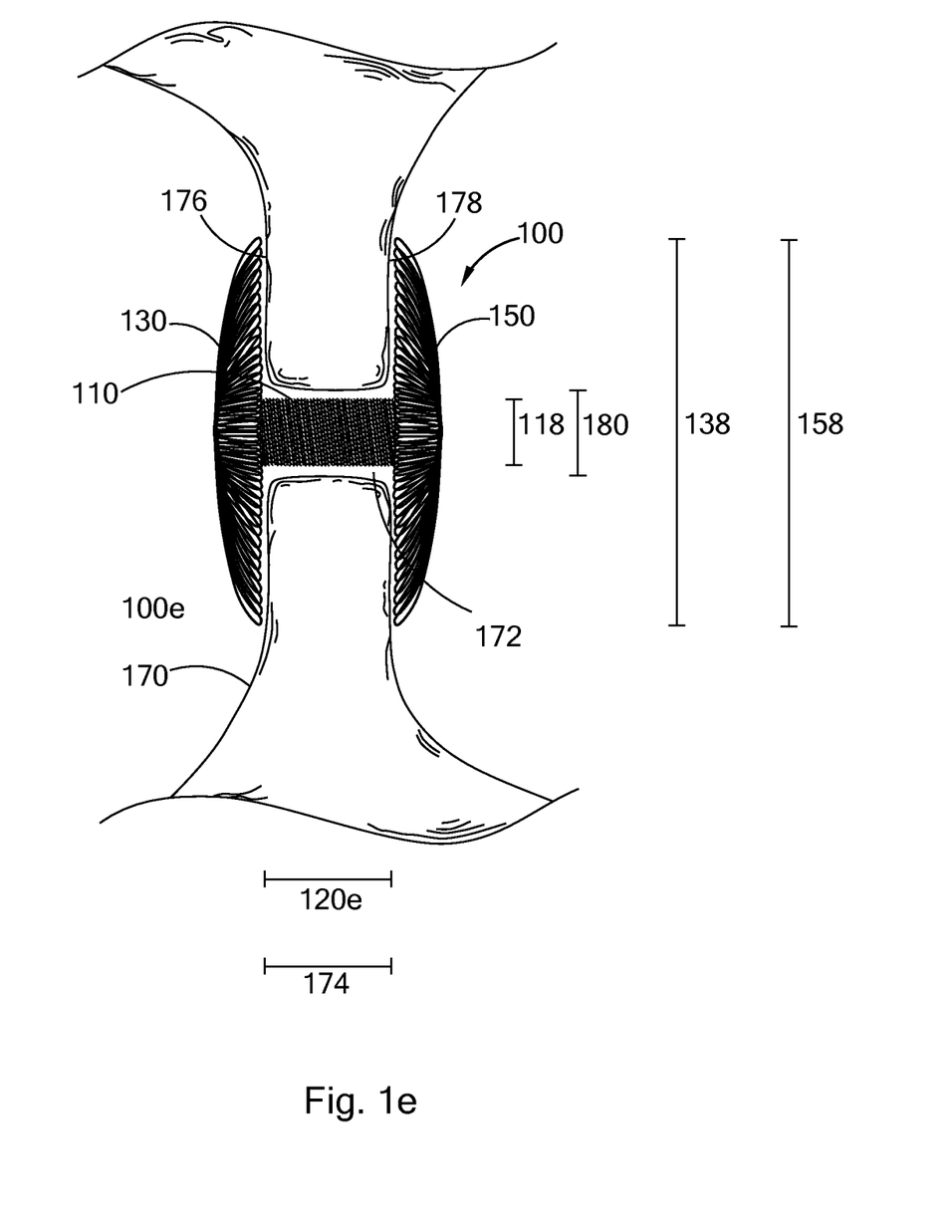
FIG. 1e is an environmental view of the occlusion device of FIG. 1a deployed in an opening in accordance with some embodiments of the present disclosure.

FIG. 1e illustrates the occlusion device 100 in a deployable configuration 100e while deployed in an opening 172 in a body tissue 170 in accordance with some embodiments of the present disclosure. The body tissue 170 may be an interatrial septum and the opening 172 may be a septal defect such as an ASD or PFO, for example. In another example, the body tissue 170 may be an interventricular septum and the opening 172 may be a septal defect such as a VSD. Those skilled in the art will recognize that the occlusion device 100 may be deployed in any body tissue with a defect that causes undesired fluid communication between cavities on either side of the body tissue. For example, the occlusion device 100 may be deployed in a PDA, which is an undesired shunt providing fluid communication between an aortic arch and a pulmonary artery. Generally, the occlusion device 100 may be applied to openings having any fractional, decimal or integral value between 2 and 12 millimeters, for example.

The occlusion device 100 may be configured to fit the opening 172. In some embodiments, the preset length 120 of the middle portion 110 may be less than a width 174 of the opening 172 and body tissue 170. Before deployment (not pictured), in order to fit through the opening 172, the occlusion device 100 may achieve a deployable configuration 100e by axially expanding the middle portion 110 to an axially expanded length 120b as in FIG. 1b, and by radially contracting the distal portion 130 to a radially contracted distal diameter 138d and the proximal portion 150 to a radially contracted proximal diameter 158d as in FIG. 1d. The axially expanded length 120b may be substantially equal to or slightly greater than the width 174 of the opening 172 and body tissue 170. The radially contracted distal and proximal diameters 138d and 158d may be less than a diameter of a lumen of an outer sheath, and the diameter of the outer sheath may be less than an opening diameter 180 of the opening 172. The function of the outer sheath will be explained in more detail in the paragraphs referencing FIGS. 2a, 2b, and 3. The deployable configuration 100e is not limited to the embodiments described herein. One skilled in the art will recognize other ways to achieve a deployable configuration 100e for deployment at the opening 172.

When deployed and no external forces are applied, the distal portion 130 and the proximal portion 150 respectively apply gradual, consistent pressures, without clamping down, to a distal side 176 and a proximal side 178 of the body tissue 170 due to the tendency of the middle portion 110 to contract. The pressure may result, for example, from an inward torque, causing the middle portion 110 to contract and thus the distal portion 130 and the proximal portion 150 to move closer together. For certain body tissues 170, the pressure may cause the width 174 of the opening 172 and body tissue 170 to decrease. While deployed, the middle portion 110 may have a deployed length 120e of a deployable configuration 100e that is less than or equal to the axially expanded length 120b and greater than the preset middle length 120.

The occlusion device 100 may be adaptable to a short or long tunnel width 174 of the opening 172, because the middle portion 110 may be expanded or contracted to fit the width 174, while substantially maintaining the preset middle diameter 118, or deforming to a lesser extent than if the middle portion 110 was formed of woven and braided wires, to ensure that the middle portion 110 does not cause further damage to the opening.

Figure 2A:
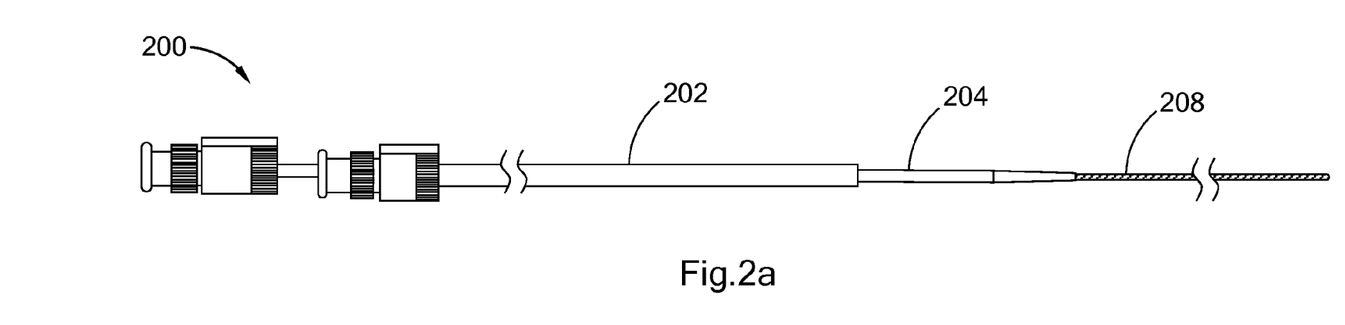
FIG. 2a a side view of a delivery and retrieval assembly for use with an occlusion device in accordance with some embodiments of the present disclosure.
Figure 2B:
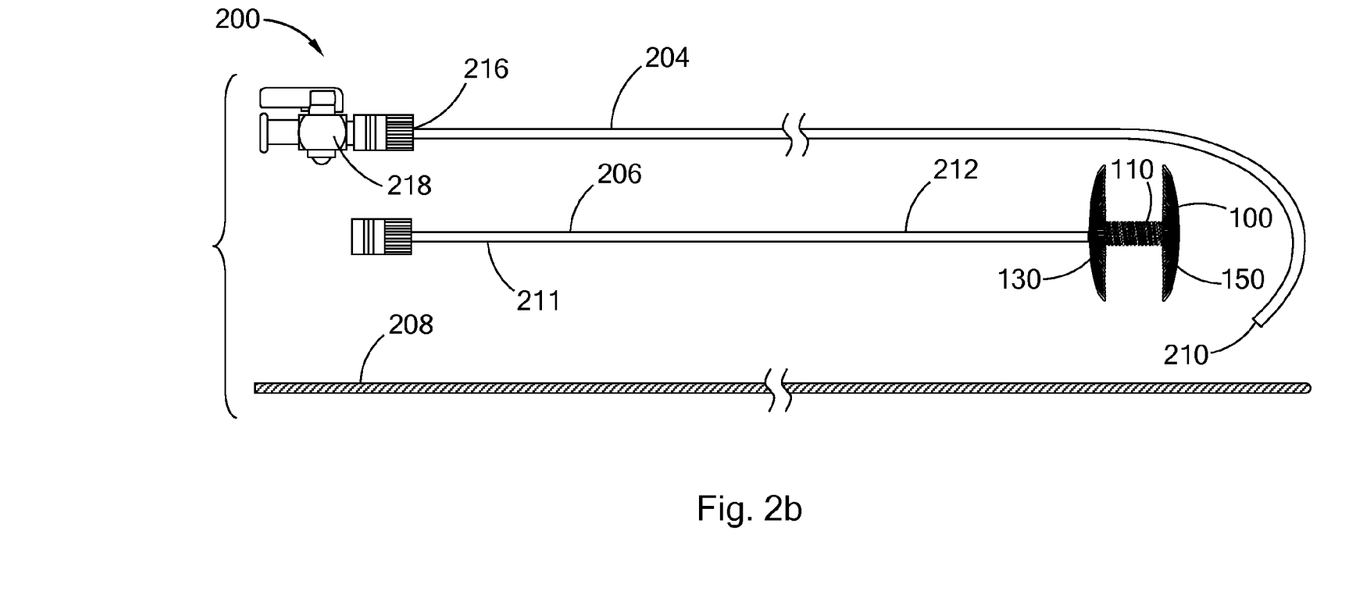
FIG. 2b is an exploded view of the delivery and retrieval assembly of FIG. 2a in accordance with some embodiments of the present disclosure.

FIGS. 2a and 2b depict a delivery assembly 200 for introducing and retrieving the occlusion device 100 for occluding an opening in a body tissue in accordance with some embodiments of the present disclosure. However, one skilled in the art will recognize that other delivery assemblies may be used for introducing and retrieving the occlusion device 100 for occluding an opening in a body tissue. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention. The introducer sheath 202 may have any suitable size, for example, between about seven-french to fourteen-french. The introducer sheath 202 serves to allow the outer sheath 204 and an inner member or catheter 206 to be percutaneously inserted to a desired location in the body tissue, cavity or vessel. The inner member may also include, for example, a stylet. The introducer sheath 202 receives the outer sheath 204 and provides stability to the outer sheath 204 at a desired location of the body tissue, cavity or vessel. For example, the introducer sheath 202 is held stationary within the body tissue, cavity or vessel, and adds stability to the outer sheath 204, as the outer sheath 204 is advanced through the introducer sheath 202 into an opening. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the opening. The wire guide 208 provides the outer sheath 204 with a path to follow as it is advanced within the body tissue, cavity or vessel. The size of the wire guide 208 is based on the inside diameter of the outer sheath 204 and the diameter of the target opening.

When the distal end 210 of the outer sheath 204 is at the desired location within the opening, the wire guide 208 is removed and the occlusion device 100, having its proximal portion 130 contacting a distal portion 212 of the inner catheter 206, is inserted into the outer sheath 204. The inner catheter 206 is advanced through the outer sheath 204 for deployment of the occlusion device 100 through the distal end 210 to occlude the opening. The catheter 206 extends from a proximal portion 211 to a distal portion 212 and is configured for axial movement relative to the outer sheath 204. In this example, the distal portion 212 is shown adjacent to the occlusion device 100 in the preset configuration 100a before introduction into the outer sheath 204. Thus, before deployment, the occlusion device 100 is coaxially disposed within the lumen of the outer sheath 204 and removably coupled to the distal portion 212 of the catheter 206, or in the alternative, the occlusion device 100 is merely pushed by, but not coupled to, the distal portion 212 of the catheter 206. The outer sheath 204 and catheter 206 may be configured to hold the middle portion 110 of the occlusion device 100 at the axially expanded length 120b.

The outer sheath 204 further has a proximal end 216 and a hub 218 to receive the inner catheter 206 and occlusion device 100 to be advanced therethrough. The size of the outer sheath 204 is based on the size of the body tissue, cavity vessel in which it percutaneously inserts, the size of the opening, and/or the size of the occlusion device 100.

In this embodiment, the occlusion device 100 and inner catheter 206 are coaxially advanced through the outer sheath 204, following removal of the wire guide 208, in order to position the occlusion device 100 to occlude the opening. The occlusion device 100 is guided through the outer sheath 204 by the inner catheter 206, preferably from the hub 218, and exits from the distal end 210 of the outer sheath 204 at a location within the opening. Thus, the occlusion device 100 is deployable through the distal end 210 of the outer sheath 204 by means of axial relative movement of the catheter 206. In order to more easily deploy the occlusion device 100 into the body vessel, the occlusion device 100 may have a slippery coating, such as Silicone or slipcoating.

Likewise, this embodiment may also retrieve the occlusion device 100 by positioning the distal end 210 of the outer sheath 204 adjacent the deployed device 100 in the vasculature. The inner catheter 206 is advanced through the outer sheath 204 until the distal portion 212 protrudes from the distal end 210 of the outer sheath 204. The distal portion 212 is coupled to a proximal end of the occlusion device 100, after which the inner catheter 206 is retracted proximally, drawing the occlusion device 100 into the outer sheath 204. The deployment and removal of the occlusion device 100 is described in more detail in the paragraphs referencing FIG. 3.

Figure 3:
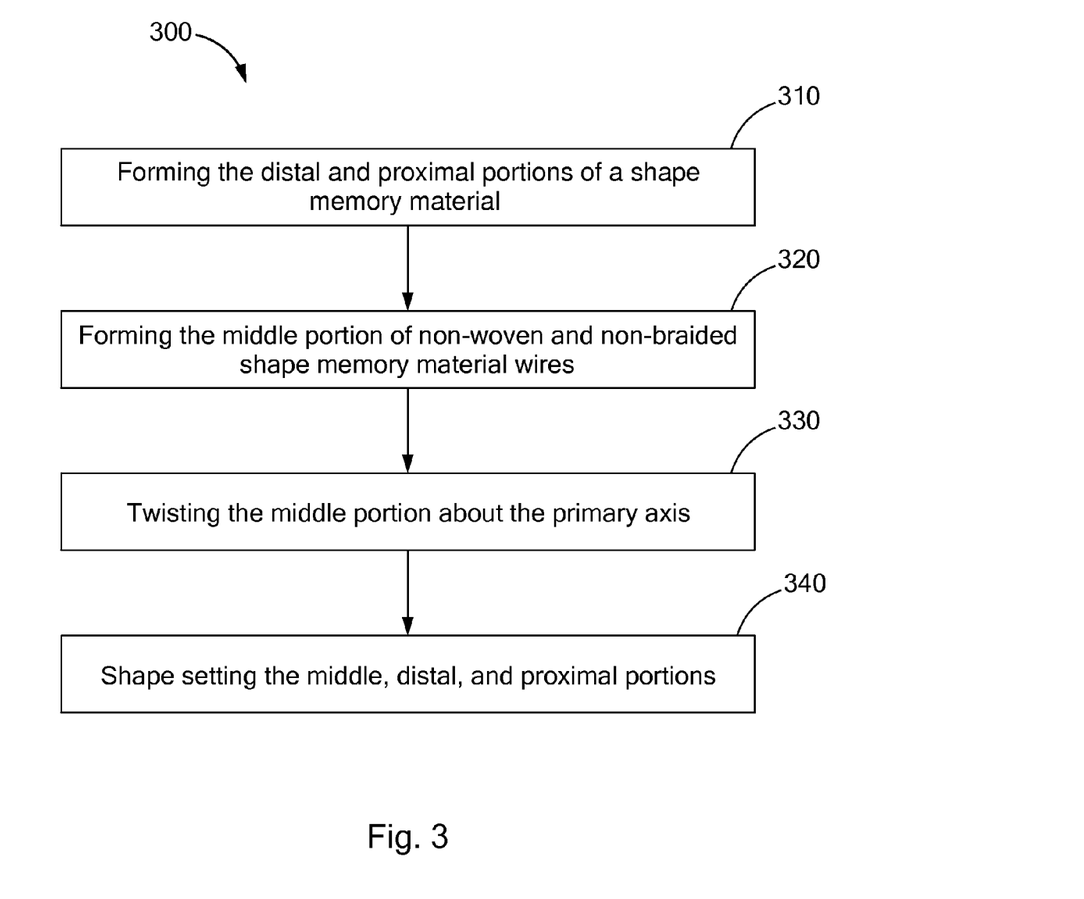
FIG. 3 is a flowchart depicting a method of forming an occlusion device for occluding an opening in a body tissue in accordance with some embodiments of the present disclosure.

FIG. 3 illustrates a method 300 of forming an occlusion device for occluding an opening in a body tissue in accordance with some embodiments of the present disclosure. The ordering of the steps presented herein is merely one implementation of the method 300. Those skilled in the art will recognize that the ordering may be varied, that some steps may occur simultaneously, that some steps may be omitted, and that further steps may be added. In block 310, a distal portion and a proximal portion of the occlusion device may be formed of a shape memory material. The shape memory material may comprise woven and/or braided wires. In block 320, a middle portion of the occlusion device may be formed of non-woven and non-braided shape memory material wires. The middle portion may have a distal end attached to the distal portion and extending to an opposing proximal end attached to the proximal portion to define a longitudinal axis. In block 330, the middle portion may be twisted along the longitudinal axis. In block 340, the distal, proximal, and middle portions may be shape set to respectively establish a preset distal diameter, a preset proximal diameter, and a preset twisted middle diameter. The preset middle diameter may be less than each of the preset distal and proximal diameters. Each of the preset distal, proximal, and middle diameters may be perpendicular to the longitudinal axis.

Figure 4:
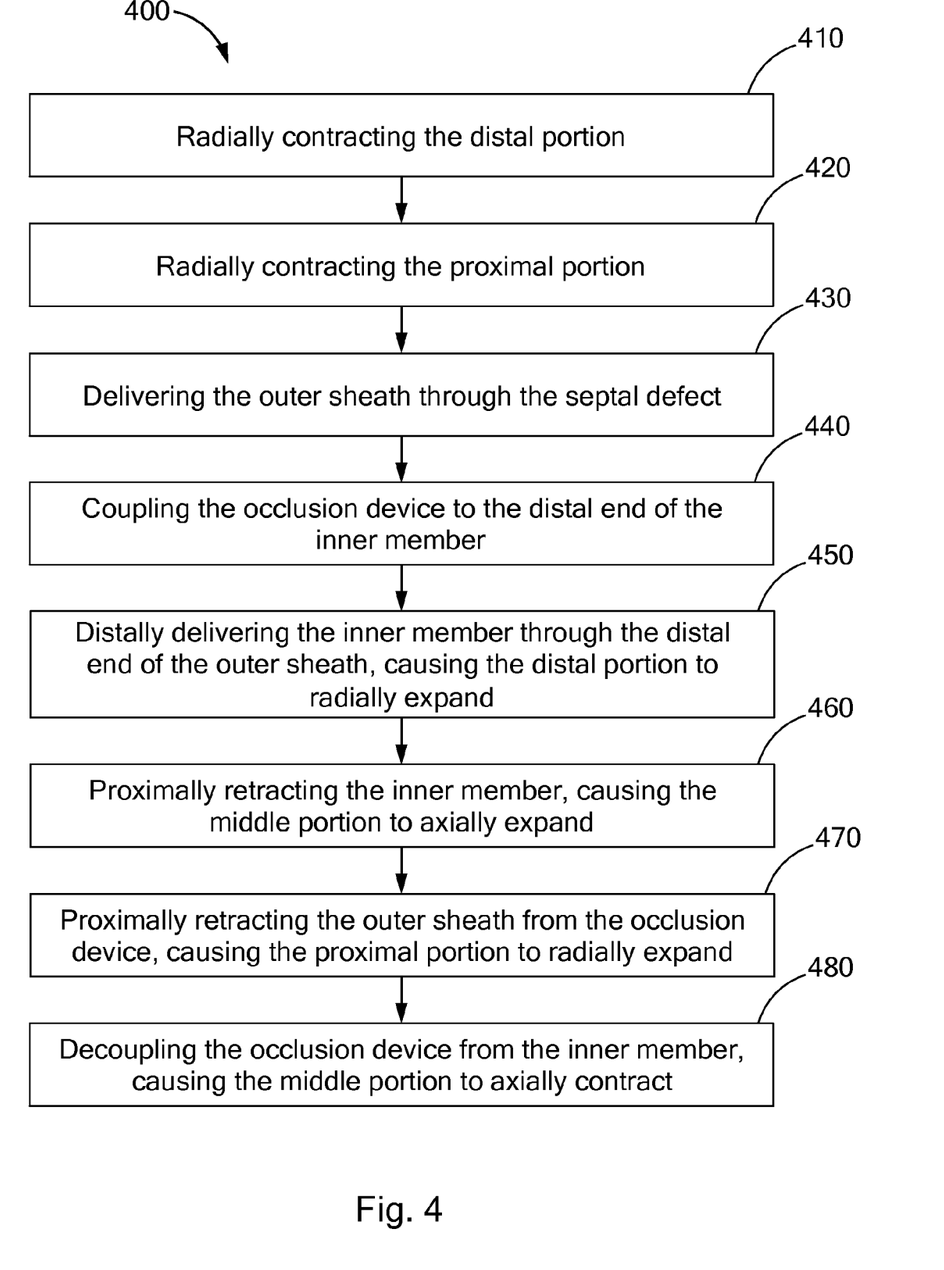
FIG. 4 is a flowchart depicting a method for occluding an opening in a body tissue with the occlusion device of FIGS. 1a to 1e and the delivery apparatus of FIGS. 2a to 2b in accordance with some embodiments of the present disclosure.

FIG. 4 illustrates a method 400 for occluding an opening in a body tissue with the occlusion device of FIGS. 1a to 1e and the delivery apparatus of FIGS. 2a and 2b in accordance with some embodiments of the present disclosure. The ordering of the steps presented herein is merely one implementation of the method 400. Those skilled in the art will recognize that the ordering may be varied, that some steps may occur simultaneously, that some steps may be omitted, and that further steps may be added.

Blocks 410 to 420 together disclose how the occlusion device may be collapsed into the collapsed configuration. One skilled in the art will recognize, however, that the collapsed configuration can be achieved through other methods. In block 410, the distal portion may be radially contracted with respect to the longitudinal axis from the preset distal diameter to the radially contracted distal diameter. In block 420, the proximal portion may be radially contracted with respect to the longitudinal axis from the preset proximal diameter to the radially contracted proximal diameter. The distal and proximal portions may radially contract by being placed in an outer sheath that has a lumen diameter less than the preset distal and proximal diameters.

Blocks 430 to 450 together disclose delivering the occlusion device to the opening. One skilled in the art will recognize, however, that the occlusion device may be delivered to the opening through other methods. In block 430, the outer sheath may be distally delivered through the opening until the distal end of the outer sheath reaches a distal end of the opening. In block 440, the occlusion device may be coupled or placed adjacent to the distal end of the inner member. In block 450, the inner member may be distally delivered through the lumen of the outer sheath until the distal portion of the occlusion device protrudes distally from the distal end of the outer sheath, causing the distal portion of the occlusion device to radially expand with respect to the longitudinal axis, from the radially contracted distal diameter to the preset distal diameter.

Blocks 460 to 480 together disclose how the occlusion device may be deployed at the opening. One skilled in the art will recognize, however, that the occlusion device may be deployed at the opening through other methods. In block 460, the inner member, while coupled to the occlusion device, may be proximally retracted, causing the middle portion to axially expand along the longitudinal axis from the preset middle length to the axially expanded middle length, wherein the preset middle length is less than a width of the body tissue and the axially expanded middle length is at least the width of the body tissue. In block 470, the outer sheath may be proximally retracted from the occlusion device, causing the proximal portion of the occlusion device to radially expand with respect to the longitudinal axis from the radially contracted proximal diameter to the preset proximal diameter. In block 480, the occlusion device may be decoupled from the distal end of the inner member, causing the middle portion to axially contract along the longitudinal axis from the axially expanded middle length to a deployed middle length, and causing the distal and proximal portions to respectively apply gradual, consistent pressures, without clamping down, to distal and proximal sides of the body tissue due to a tendency of the middle portion to contract. The deployed middle length is equal to the width of the body tissue. The pressures may result, for example, from inward torques, causing the middle portion to contract and thus the distal portion and the proximal portion to move closer together. Alternatively, the inner member may be distally advanced to axially contract the middle portion along the longitudinal axis from the axially expanded middle length to the deployed middle length, after which the occlusion device may be decoupled from the distal end of the inner member.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

What is claimed is:

1. An occlusion device for occluding an opening in a body tissue, the occlusion device comprising:
a middle portion having a distal end extending to an opposing proximal end to define a longitudinal axis of the device, the middle portion being formed of non-woven wires and twisted about the longitudinal axis, the middle portion having a preset middle diameter;
a distal portion that is attached to the distal end of the middle portion, the distal portion having a preset distal diameter and being made of a shape memory material;
a proximal portion that is attached to the proximal end of the middle portion, the proximal portion having a preset proximal diameter and being made of a shape memory material; and
wherein the preset middle diameter is less than each of the preset distal and proximal diameters, and wherein each of the preset middle, distal, and proximal diameters is perpendicular to the longitudinal axis.

2. The occlusion device of claim 1 wherein the middle portion is made of a shape memory material, and wherein the middle portion is configured to axially expand along the longitudinal axis from a preset middle length to an expanded middle length upon application of an external axial expanding force, and to axially contract along the longitudinal axis from the expanded middle length to the preset middle length upon release of the external axial expanding force.

3. The occlusion device of claim 2 wherein the preset middle length is configured to be less than a width of the body tissue and the expanded middle length is configured to be at least the width of the body tissue, and wherein releasing the external axial expanding force while the middle portion has the expanded middle length causes the distal portion to apply a first pressure to a distal side of the body tissue and the proximal portion to apply a second pressure to a proximal side of the body tissue.

4. The occlusion device of claim 1 wherein the non-woven wires are formed of nitinol.

5. The occlusion device of claim 1 wherein the non-woven wires are parallel to one another, and wherein the twisting of the middle portion about the longitudinal axis causes the non-woven wires to form spirals that extend about the longitudinal axis.

6. The occlusion device of claim 1 wherein the middle portion has a tubular shape with a substantially constant diameter along the longitudinal axis.

7. The occlusion device of claim 1 wherein the distal portion comprises a distal set of wires, the distal set of wires being one of woven and braided, and wherein the proximal portion comprises a proximal set of wires, the proximal set of wires being one of woven and braided.

8. The occlusion device of claim 1 wherein each of the distal portion and the proximal portion have a disc shape.

9. The occlusion device of claim 8 wherein each interior end of the distal portion and the proximal portion has one of a flat and concave surface, each interior end being respectively configured to attach to a distal side and a proximal side of the body tissue.

10. A method for occluding an opening in a body tissue with an occlusion device, comprising:
    providing the occlusion device deployed from an inner member at the opening in the body tissue, the occlusion device comprising:
        a middle portion having a distal end extending to an opposing proximal end to define a longitudinal axis of the device, the middle portion being formed of non-woven wires and twisted about the longitudinal axis, the middle portion having a preset middle diameter;
        a distal portion that is attached to the distal end of the middle portion, the distal portion having a preset distal diameter and being made of a shape memory material;
        a proximal portion that is attached to the proximal end of the middle portion, the proximal portion having a preset proximal diameter and being made of a shape memory material;
        wherein the preset middle diameter is less than each of the preset distal and proximal diameters, and wherein each of the preset middle, distal, and proximal diameters is perpendicular to the longitudinal axis;
    collapsing the occlusion device into a collapsed configuration; and
    delivering the occlusion device to the opening.

11. The method of claim 10 wherein collapsing the occlusion device into a collapsed configuration comprises:
    contracting the distal portion radially with respect to the longitudinal axis from the preset distal diameter to a radially contracted distal diameter; and
    contracting the proximal portion radially with respect to the longitudinal axis from the preset proximal diameter to a radially contracted proximal diameter.

12. The method of claim 11 wherein delivering the occlusion device to the opening comprises delivering an outer sheath distally through the opening until a distal end of the outer sheath reaches a distal end of the opening.

13. The method of claim 12 wherein delivering the occlusion device to the opening further comprises delivering the inner member distally through a lumen of the outer sheath until the distal portion of the occlusion device protrudes from the distal end of the outer sheath, causing the distal portion of the occlusion device to radially expand with respect to the longitudinal axis, from the radially contracted distal diameter to the preset distal diameter.

14. The method of claim 13 further comprising retracting the outer sheath from the occlusion device, causing the proximal portion of the occlusion device to radially expand with respect to the longitudinal axis from the radially contracted proximal diameter to the preset proximal diameter.

15. The method of claim 14 wherein delivering the occlusion device to the opening further comprises coupling the occlusion device to a distal end of the inner member.

16. The method of claim 15 further comprising:
    retracting the inner member proximally while the inner member is coupled to the occlusion device and while the distal portion having the preset distal diameter is deployed at the distal end of the opening, causing the middle portion to axially expand along the longitudinal axis from a preset middle length to an axially expanded middle length, wherein the preset middle length is less than a width of the body tissue and the axially expanded middle diameter is at least the width of the body tissue; and
    decoupling the occlusion device from the distal end of the inner member while the outer sheath is retracted from the occlusion device, causing the middle portion to axially contract along the longitudinal axis from the axially expanded middle length to a deployed middle length, and causing the distal portion to apply a first pressure to a distal side of the body tissue and the proximal portion to apply a second pressure to a proximal side of the body tissue, wherein the deployed middle length is equal to the width of the body tissue.

17. The method of claim 10 wherein the non-woven wires are parallel to one another, and wherein the twisting of the middle portion about the longitudinal axis causes the non-woven wires to form spirals that extend along the longitudinal axis.

18. The method of claim 10 wherein the middle portion has a tubular shape with a substantially constant diameter along the longitudinal axis.

19. A delivery assembly for placing and retrieving an occlusion device for occluding an opening in a body tissue, the assembly comprising:
    an outer sheath having a tubular body extending from a proximal part to a distal part and the tubular body including a sheath lumen extending therethrough;
    an inner member extending from a proximal portion to a distal portion, the inner member being disposed within the sheath lumen and configured for axial movement relative to the outer sheath;

the occlusion device being coaxially disposed within the sheath lumen and removably coupled to the distal portion of the inner member and deployable through the distal part of the outer sheath by means of the relative axial movement of the inner member, the occlusion device comprising:

a middle portion having a distal end extending to an opposing proximal end to define an longitudinal axis of the device, the middle portion being formed of non-woven wires and twisted about the longitudinal axis, the middle portion having a preset middle diameter;

a distal portion that is attached to the distal end of the middle portion, the distal portion having a preset distal diameter and being made of a shape memory material;

a proximal portion that is attached to the proximal end of the middle portion, the proximal portion having a preset proximal diameter and being made of a shape memory material;

wherein the middle diameter is less than each of the preset distal diameter and proximal diameters, and wherein each of the preset middle, distal, and proximal diameters is perpendicular to the longitudinal axis.

20. A method of forming an occlusion device for occluding an opening in a body tissue, comprising:

forming from a shape memory material a distal portion of the occlusion device and a proximal portion of the occlusion device;

forming from non-woven shape memory material wires a middle portion of the occlusion device, the middle portion having a distal end attached to the distal portion and extending to an opposing proximal end attached to the proximal portion to define a longitudinal axis;

twisting the middle portion about the longitudinal axis; and shape setting the distal portion to establish a preset distal diameter, the proximal portion to establish a preset proximal diameter, and the twisted middle portion to establish a preset middle diameter, wherein the middle diameter is less than each of the preset distal and proximal diameters, and wherein each of the preset distal, proximal, and middle diameters is perpendicular to the longitudinal axis.

21. An occlusion device for occluding an opening in a body tissue, the occlusion device comprising:

a middle portion having a distal end extending to an opposing proximal end to define a longitudinal axis of the device, the middle portion being formed of non-woven wires and twisted about the longitudinal axis, the middle portion having a preset middle diameter;

a distal portion that is attached to the distal end of the middle portion, the distal portion having a preset distal diameter and being made of a shape memory material;

a proximal portion that is attached to the proximal end of the middle portion, the proximal portion having a preset proximal diameter and being made of a shape memory material;

wherein the preset middle diameter is less than each of the preset distal and proximal diameters, and wherein each of the preset middle, distal, and proximal diameters is perpendicular to the longitudinal axis; and wherein the middle portion may be axially expanded and contracted while substantially maintaining the preset middle diameter.

* * * * *